US00PP10174P

United States Patent [19]

Zaiger et al.

[11] Patent Number: Plant 10,174

[45] Date of Patent: Jan. 6, 1998

[54] NECTARINE TREE 'ARCTIC BLAZE'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 717,009

[22] Filed: Sep. 20, 1996

[51] Int. Cl.[6] ..... A01H 5/00

[52] U.S. Cl. ..... Plt./40.1

[58] Field of Search ..... Plt./40.1

*Primary Examiner*—James R. Feyrer

[57] ABSTRACT

A new and distinct variety of nectarine *Prunus persica*, tree which has the following unique combination of outstanding features that are desirable in a new variety:

1. Heavy and regular production of large size fruit.
2. Fruit with excellent flavor and eating quality.
3. Fruit with firm white flesh with good handling and shipping quality.
4. Fruit that will stay firm 10 to 12 days after maturity (shipping ripe).
5. Relatively uniform maturity of fruit throughout the tree.
6. Vigorous, upright growth.

1 Drawing Sheet

ORIGIN OF THE VARIETY

The present new variety of nectarine tree was originated by us in our experimental orchard located near Modesto, Calif., as a first generation cross between two selected seedlings with field identification numbers 23R236 and 63EC404. The maternal parent (23R236) originated from a nectarine of unknown parentage crossed with a selected seedling originating from a cross of O'Henry Peach (U.S. Plant Pat. No. 2,964) and Giant Babcock Peach (U.S. Plant Pat. No. 1,353). The paternal parent (63EC404) originated from a cross of two selected seedlings, one from a Sunred Nectarine (non-patented) crossed with Crimson Gold Nectarine (U.S. Plant Pat. No. 2,825), the other from an Autumn Grand Nectarine (U.S. Plant Pat. No. 2,894) crossed with Rhone Gold Nectarine (non-patented). The present variety was selected from a large number of first generation seedlings planted and grown under close and careful observation, during which time we recognized its desirable characteristics described above and selected the variety for asexual propagation and commercialization.

ASEXUAL REPRODUCTION OF THE VARIETY

Asexual reproduction of the new and distinct variety was by budding, as performed by us in our experimental orchard located near Modesto, Calif., which shows that all characteristics of the tree and its fruit are established and transmitted through succeeding asexual propagations and run true to the original tree in all respects.

SUMMARY OF THE VARIETY

A new and distinct variety of nectarine tree which is of large size; vigorous, upright growth; and being a productive and regular bearer of large, firm, white flesh, clingstone fruit. The fruit is further characterized by having a mild, sweet, subacid flavor with excellent eating quality; having firm flesh with good handling and shipping quality; and holding firm on the tree 10 to 12 days after maturity (shipping ripe). In comparison to Arctic Queen Nectarine (U.S. Plant Pat. No. 8,094), the fruit of the new variety is larger in size and is 7 to 8 days later in maturity.

DESCRIPTION OF THE PHOTOGRAPH

The accompanying color photographic illustration shows typical specimens of the foliage and fruit of the present new variety of nectarine tree. The photographic illustration is of the upper and lower surface of the leaves, and of the exterior and a sectional view of a fruit. divided in the suture plane to reveal flesh coloration, pit cavity and a stone remaining in place. The photograph was taken shortly after the fruit was picked at maturity (firm ripe) and the colors are as nearly true as is reasonably possible in a color representation of this type.

DESCRIPTION OF THE VARIETY

The following is a detailed botanical description of the present new variety of nectarine tree, its flowers, foliage and fruit are based on observations of specimens grown near Modesto, Calif., with color terminology (except those in common terms) in accordance with Reinhold Color Atlas by A. Kornerup and J. H. Wanshcer.

Tree:
- *Size.*—Large.
- *Vigor.*—Vigorous.
- *Form.*—Upright.
- *Density.*—Medium dense.
- *Production.*—Productive.
- *Bearer.*—Regular.

Trunk:
- *Size.*—Large.
- *Texture.*—Medium shaggy.
- *Color.*—Brown to dark brown (6-E-6) to (6-F-6).

Branches:
- *Size.*—Medium.
- *Texture.*—Smooth to medium rough, varies with age of growth.
- *Lenticels.*—Numerous. Medium to large size.
- *Color.*—Light brown to brown (6-D-8) to (6-E-8).

Leaves:
- *Size.*—Large. Average length 6". Average width 1⅝".
- *Form.*—Lanceolate, pointed.
- *Texture.*—Smooth.
- *Thickness.*—Medium.
- *Margin.*—Crenate.
- *Petiole.*—Medium length.

Medium thickness.
- *Glands.*—Reniform. Number varies from 1 to 3. Average number 2. Medium size. Located on upper portion of the petiole and lower portion of the leaf blade.

*Color.*—Upper surface—green to dark green (28-E-8 ) to (28-F-8 ). Lower surface—grayish green to green (28-D-7 ) to (28-E-7 ).

Flower buds:

*Size.*—Medium to large.

*Form.*—Plump.

*Pubescence.*—Pubescent.

Flowers:

*Size.*—Large, showy.

*Blooming period.*—Date of first bloom: Mar. 3, 1994. Date of full bloom: Mar. 7, 1994.

*Pollen.*—Present, self-fertile.

*Color.*—Pink.

Fruit:

*Maturity when described.*—Firm ripe.

*Date of first picking.*—Aug. 2, 1994.

*Date of last picking.*—Aug. 8, 1994. Maturity varies slightly with climatic conditions.

*Size.*—Large. Average diameter axially 3". Average transversely in suture plane 3".

*Form.*—Nearly globose.

*Suture.*—Shallow, extends from base to apex.

*Ventral surface.*—Nearly round, very slightly lipped.

*Cavity.*—Rounded to slightly elongated in suture plane. Average depth ⅜". Average breadth ⅞".

*Base.*—Retuse.

*Apex.*—Usually very small pistil point, varies from small pistil point to round.

Flesh:

*Ripens.*—Evenly.

*Texture.*—Firm.

*Fibers.*—Few, small, tender.

*Juice.*—Moderate.

*Aroma.*—Moderate.

*Amygdalin.*—Undetected

*Flavor.*—Excellent, mild, sweet, subacid.

*Eating quality.*—Excellent.

*Color.*—White to pinkish white (7-A-1) to (7-A-3). Pit cavity—red to blood red (10-D-8) to (10-E-8). Bleeding into flesh around pit cavity.

Skin:

*Thickness.*—Medium.

*Texture.*—Medium, tenacious to the flesh.

*Tendency to crack.*—None.

*Down.*—Wanting.

*Color.*—White to yellowish white ground color (5-A-1) to (5-A-3). Nearly overspread with lake red to garnet red (9-C-8) to (9-D-8). Ground color showing through red, giving a speckled, randomly spaced mottled pattern.

Stone:

*Type.*—Clingstone.

*Size.*—Large. Average length 1½". Average width 1 1/16". Average thickness ¾".

*Form.*—Ovate to obovate.

*Base.*—Varies from straight to rounded.

*Apex.*—Acuminate.

*Sides.*—Equal to unequal.

*Surface.*—Irregularly furrowed toward apex, pitted toward base, pit cavities vary from round to elongated.

*Ridges.*—Rounded.

*Tendency to split.*—None.

*Color.*—Brownish red to reddish brown (9-E-8) to (9-F-8).

Use: Dessert.

*Market.*—Local and long distance.

Keeping Quality: Good.

Shipping Quality: Good.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth and being a productive and regular bearer of large size, white flesh, clingstone fruit with excellent flavor and eating quality; the fruit is further characterized by holding firm on the tree 10 to 12 days after maturity (shipping ripe), having good handling and shipping quality and, in comparison to Arctic Queen Nectarine (U.S. Plant Pat. No. 8,094), the fruit is larger in size and is 7 to 8 days later in maturity.

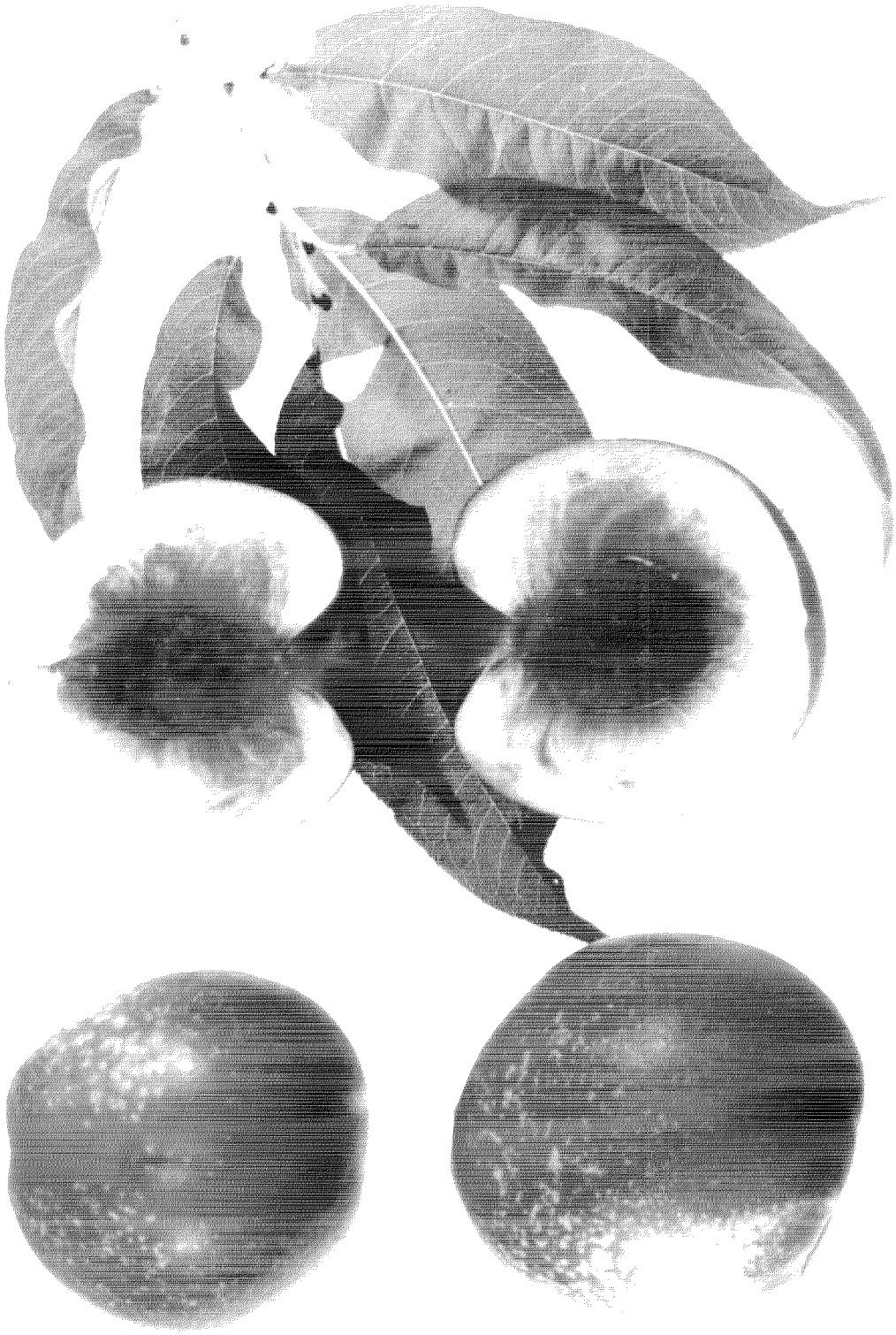

* * * * *